United States Patent [19]
Schneider

[11] Patent Number: 5,297,437
[45] Date of Patent: Mar. 29, 1994

[54] DEVICE FOR MANOMETRIC MEASUREMENT OF THE ESOPHAGUS

[76] Inventor: Joachim Schneider, Hoppe-Seyler-Str. 3, 7400 Tübingen, Fed. Rep. of Germany

[21] Appl. No.: 865,971
[22] Filed: Apr. 9, 1992
[51] Int. Cl.[5] .............................................. G01L 9/00
[52] U.S. Cl. ..................................... 73/705; 178/780; 250/231.19; 356/352
[58] Field of Search ..................... 73/705; 250/231.19; 356/352; 128/667, 748, 780

[56] References Cited

U.S. PATENT DOCUMENTS

| | | | |
|---|---|---|---|
| 3,480,003 | 11/1969 | Crites | 128/748 |
| 3,939,823 | 2/1976 | Kaye et al. | 128/780 |
| 4,803,992 | 2/1989 | Lemelson | 128/748 |
| 4,924,877 | 5/1990 | Brooks | 128/667 |
| 4,991,590 | 2/1991 | Shi | 73/705 |
| 5,018,529 | 5/1991 | Tenerz et al. | 73/705 |

Primary Examiner—Donald O. Woodiel
Attorney, Agent, or Firm—Hopkins & Thomas

[57] ABSTRACT

A device for manometric measurement of the oesophagus has a catheter with a pressure sensor and a recording unit with a light source for monochromatic and coherent light, and a counting unit for light pulses. The pressure sensor is constructed as a Fabry Perot measuring section and has a pliable optical fiber embedded in elastic base material. The optical fiber is connected via a fiber-optic light guide to the recording unit (3). One end (6) of the optical fiber (5) is metal-coated and the other end (7) is partially metal-coated and connected to the fiber-optic light guide (8). The fiber-optic light guide (8) conveys not only the light from the light source to the optical fiber but also the light pulses from the optical fiber to the counting unit.

12 Claims, 3 Drawing Sheets

DEVICE FOR MANOMETRIC MEASUREMENT OF THE ESOPHAGUS

FIELD OF THE INVENTION

The invention refers to a device for the manometric measurement of the oesophagus which has a catheter with a pressure sensor and a recording unit which has a light source for monochromatic and coherent light as well as a counting unit for light pulses, whereby the pressure sensor has a pliable optical fiber embedded in an elastic base material and is constructed as a Fabry Perot measuring section which is connected to the recording unit via a fiber-optic light guide. The manometric measurement of the oesophagus, i.e. the recording of pressures and forces in the gullet, serves for indicating peristaltic swallowing contractions of the gullet musculature in healthy patients or, however, affections of the oesophagus motility. Of particular interest at the present time are the activities of the lower oesophagus sphincter which, however, owing to changes in position caused by breathing and swallowing, is difficult to examine.

BACKGROUND OF THE INVENTION

A device of the above-described type is known from the article "The fibre Fabry Perot sensor" (J. Scheider et al., Clin. Phys. Physiol. Meas., 1990, vol. 11, No. 4, 319 through 325). The optical fiber of the pressure sensor is in this case connected via two fiber-optic light guides to the recording unit. Using the first fiber-optic light guide, light from the light source is sent into the optical fiber, and the second fiber-optic light guide serves to feed back the measuring signal from the Fabry Perot measuring section to the recording unit. Therefore, the two fiber-optic light guides are connected to the opposite ends of the optical fiber. Accordingly, the optical fiber or one of the fiber-optic light guides must be bent to a small radius and located in the catheter. Coupled with this is an extraordinary mechanical strain on the optical fiber or the fiber-optic light guide. A relatively high frequency of breakages is the result. This is diametrically opposed to the functional reliability of the device, particularly necessary when the device is to be used for lengthy examinations.

With a different device for the manometric measurement of the oesophagus, the catheter has mechanical pressure sensing elements. Piezo crystals are essential components of these pressure sensing elements. The piezo crystals of the pressure sensing elements are connected via electrical lines to a recording unit. A disadvantage with the mechanical pressure sensing elements is that they are only suitable for local measurement of pressures. This means that the pressure sensing elements must be precisely arranged at the point where the pressure which is to be measured occurs. However, this is virtually impossible during lengthy examinations, especially with manometric measurement of the lower oesophagus sphincter. The position of the musculature which seals off the stomach alters with respect to the catheter during strong breathing movements such that examining them using a mechanical pressure sensing element can no longer be undertaken.

SUMMARY OF THE INVENTION

It is the object of the invention to demonstrate a device for manometric measurement of the oesophagus which, in particular, is suitable for lengthy examinations of the oesophagus and its sphincters.

According to the invention, this is achieved in that one end of the optical fiber is metal-coated and the other end is partially metal-coated and connected to a fiber-optic light guide, and that the fiber-optic light guide not only conveys the light from the light source to the optical fiber but also the light pulse from the optical fiber to the counting unit. If the optical fiber is operated as a Fabry Perot measuring section in reflection, it is advantageous that it is not necessary to bend the optical fiber or a fiber-optic light guide. The mechanical stability of the pressure sensor is increased enormously by doing this. In contrast, its size, in particular with regard to the cross-section of the catheter, can be reduced, thus allowing examination of the oesophagus sphincter in a quasi-closed position. Further, there results from this application of an optical fiber with a metal-coated end, the advantage that only one single fiber-optic light guide is necessary for connecting the optical fiber to the recording unit. This fiber-optic light guide feeds not only the light from the light source to the optical fiber but also the measuring signal to the recording unit. For this purpose, a Y-coupler can, for example, be provided in the recording unit; the light source on the one hand and the cell unit for light pulses on the other are located on the two backward-facing arms of the Y-coupler.

For long term examinations, it is advantageous for the recording unit to have a data memory and be constructed in a portable form. The patient can, therefore, move more or less unhindered and the manometric measurement can be carried out under boundary conditions which are as natural as possible. In particular, the recording of processes which take place only infrequently is made easier. Apart from that, an essentially undisturbed food intake is possible for the patient owing to the small cross-section of the catheter, meaning that he/she does not need to remain without food during lengthy examinations.

The recording unit can have a temperature probe allocated to the light source. With nearly all light sources, the wavelength of the light emitted is dependent on the temperature of the light source. The reading occuring at the Fabry Perot measuring section, i.e. the sequence of light and dark signals, just depends, however, on the wavelength of the light used. In particular, a portable recording unit is now subjected to temperature fluctuations which are taken into account with precise analysis of the readings which occur or are compensated for by a temperature regulation of the light source right at the very beginning.

The catheter can, besides the pressure sensor, have mechanical pressure sensing elements, whereby the pressure sensor is allocated to the sphincter and the pressure sensing elements are allocated to the actual body of the oesophagus. Furthermore, the use of known pressure sensing elements in the area of the gullet have been shown to be advantageous. In this area the use of a new pressure sensor is in fact rather a disadvantage. Therefore, particular advantages are associated with a device in which the catheter not only has usual pressure sensing elements with piezo crystals but also a new pressure sensor with an optical fiber.

The catheter can have numerous pressure sensors arranged parallel and adjacent each other around the circumference of the catheter. It is known that the oesophagus sphincter has a musculature which is not arranged symmetrically about the axis of the gullet. A definition and examination of this asymmetry is possible through the use of several pressure sensors arranged parallel and adjacent each other in one plane. Advantageous in this situation is that a support, made from a material which is less elastic than the base material, is located inside the catheter between the pressure sensors. In this way, mutual coupling of the signals of the individual sensors is limited. Only the reading which corresponds to its local allocation occurs at each pressure sensor.

A digitizing facility and a multiplexer can be fitted upstream of the data memory. It is a fact that in a device with several pressure sensors, or pressure sensors and pressure sensing elements, the rational storage of actual readings presents a problem. This can be dealt with through using a digitizer facility and a multiplexer which are fitted upstream of the data memory. Here, the multiplexer triggers the individual pressure sensors or pressure sensing elements successively.

An adjustable, frequency-dependent filter can be fitted upstream of the counting unit. The readings which are of interest in manometric measurement of the oesophagus exhibit a certain frequency spectrum. Therefore, readings with other frequencies can be reliably isolated and suppressed as noise or reading errors by using a frequency-dependent filter.

The other end of the optical fiber can be partially coated by the vapor-deposition technique. By giving the fiber material a thin coating, for example, of a stainless steel, using the vapor-deposition technique, there ensues a partially light-transmissive transitional region through which it is possible to radiate light into the optical fiber while, at the same time, the light is reflected into the optical fiber with the required frequency.

The optical fiber can be of the single mode type and the fiber-optic light guide can be of the multi-mode type. In an optical fiber of the single mode type, undesired stray light is advantageously suppressed out of the system. This of course assumes that the mode of the optical fiber is precisely matched to the wavelength of the light source. However, the fiber-optic light guide must by of the multi-mode type in order to reliably conduct the light-dark signals from the Fabry Perot measuring section to the recording unit.

The optical fiber can be wrapped around the longitudinal axis of the catheter in helical form. In doing this, spring steel strips can be provided to not only secure and protect the fiber but also to guarantee the force transfer to the fiber. With a wrapped optical fiber arrangement, the effective length of the fiber exposed to the pressure of the oesophagus sphincter is particularly large. Therefore, the pressure sensor also reacts effectively to rapid changes in pressure in the region of th sphincter. Reproducible, easily recorded readings are the result.

BRIEF DESCRIPTION OF THE DRAWINGS

In the following, the invention is more closely explained and described by means of an embodiment example. It shows.

DETAILED DESCRIPTION

Figure 1:
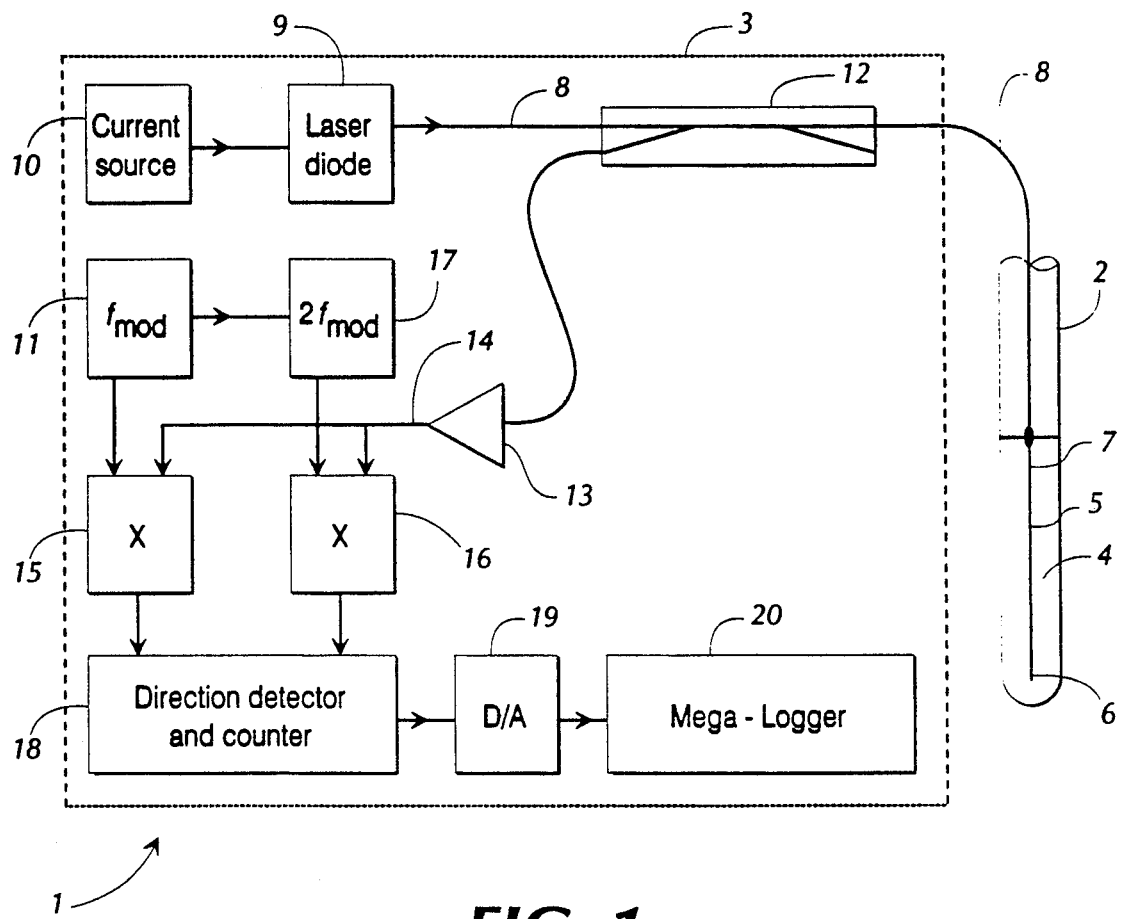
FIG. 1 is a schematic illustration of the manometer.

The device 1 for manometric measurement of the oesophagus illustrated in FIG. 1 has a catheter 2 and a recording unit 3. An optical fiber 5, embedded in elastic base material 4, is provided at the tip of the catheter 2. One end 6 of the optical fiber 5 is metal-coated. At the other end 7, the optical fiber 5 is constructed semi-pervious and connected to a fiber-optic light guide 8. The fiber-optic light guide 8 represents the connection between the catheter 2 and the recording unit 3. In this case, a light source 9, constructed as a laser diode, is provided in the recording unit 3. The light source 9 is fed by a current supply 10. Furthermore, a frequency transmitter 11 is provided which modulates the current supply 10 and therewith the light source 9 as well using the frequency fmod. Strictly speaking, the wavelength of light source 9 varies here depending on the frequency fmod. The light emitted from light source 9 is monochromatic and coherent. The light is conducted from the fiber-optic light guide 8 to the optical fiber 5. A Y-coupler 12 is provided in the fiber-optic light guide 8. A light detector 13 is attached to the other backward-facing arm of the Y-coupler 12. The output 14 of light detector 13 is connected to two lock-in amplifiers 15, 16. In doing this, the first lock-in amplifier 15 is synchronized by the frequency transmitter 11 using the frequency fmod. A frequency duplicator 17 is located between the second lock-in amplifier 16 and the frequency transmitter 11 so that the second lock-in amplifier 16 is synchronized using the frequency 2 fmod. The output signals of both lock-in amplifiers 15, 16 are recorded by a directional detector and counter 18. Thereupon, the output signals of this are digitized by a digital-to-analog converter 19 and stored in a data memory 20.

At this point the method of operation of a Fabry Perot measuring section will be briefly mentioned. Such a Fabry Perot measuring section is formed by the optical fiber 5 with the metal-coated end 6 and the semi-pervious end 7. In the Fabry Perot measuring section, monochromatic and coherent light which is radiated in is then reflected many times at the ends of the measuring section and, thereby, superimposes itself many times on the measuring section. This superimposing is, as a rule, destructive at the semi-pervious end 7 provided the optical wavelength of the Fabry Perot measuring section is a multiple of half the wavelength of the light being used. The optical path length of the Fabry Perot measuring section varies with mechanical effects acting on the optical fiber. The amount of this variation can be determined by observing and enumerating the conditions with constructive interference. If, for example, at end 7 of the optical fiber 5 ten bright (light) signals are observed, then the optical fiber 5 reached ten times half the wavelength, but five times the wavelength, of the light being used. Observing the bright signals at the semi-pervious end 7 is carried out using the fiber-optic light guide 8. Lastly, the light detector 13 is provided for observing the light or dark signals. The base material 4 serves here as a medium which repeatedly just so deviates the forces which occur that they effect a change in length of the optical fiber 5. In order to determine absolute forces or pressures, it needs to be established whether the bright signals originate from an optical fiber 5 which has been expanded or one which has been contracted again. The frequency transmitter 11, the frequency duplicator 17 and the two lock-in amplifiers 15 and 16 are provided for this purpose. The wavelength modulation at the light source 9 already leads to light-dark signals at the light detector 13 without an alteration in the optical length of the optical fiber 5. These signals appear with a frequency fmod and also a frequency 2 fmod. The light-dark signals superimposed on this through an alteration in the optical length of the optical fiber 5, can now be recognized through a phase shift with respect to the frequency of the frequency transmitter 11. Lastly, the light-dark signals are so recorded in the directional detector and counter 18 that the value of the output to the digital-to-analog converter 19 represents a measure for the absolute change in length of the optical fiber 5 and, therewith, for the force influencing the optical fiber 5 as well. The data stored sequentially in the data memory 20 reflects therefore, the temporal pressure progression at the point of the optical fiber 5 forming a pressure sensor in the oesophagus.

Figure 2:
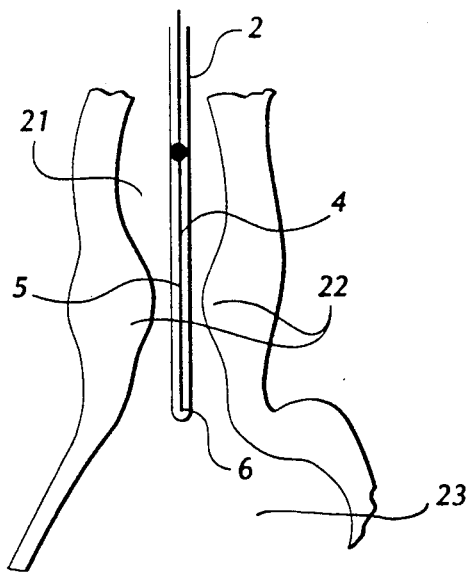
FIG. 2 is a detail of the catheter of the manometer showing how the catheter is used.

FIG. 2 shows the tip of the catheter 2 when using the device 1 according to FIG. 1. In doing this, the catheter 2 is so arranged within the oesophagus 21 that the lower oesophagus sphincter 22 acts upon the optical fiber 5 via the base material 4. Therefore, the catheter 2 reaches with its tip up into the entrance to the stomach 23. It can be seen that a shift in position of the lower oesophagus sphincter does not normally cause any harm when the catheter 2 is correctly positioned because the pressure sensor formed by the optical fiber 5 has a relatively large longitudinal extension. Consequently, the maximum pressure of the lower oesophagus sphincter is always measured.

Figure 3:
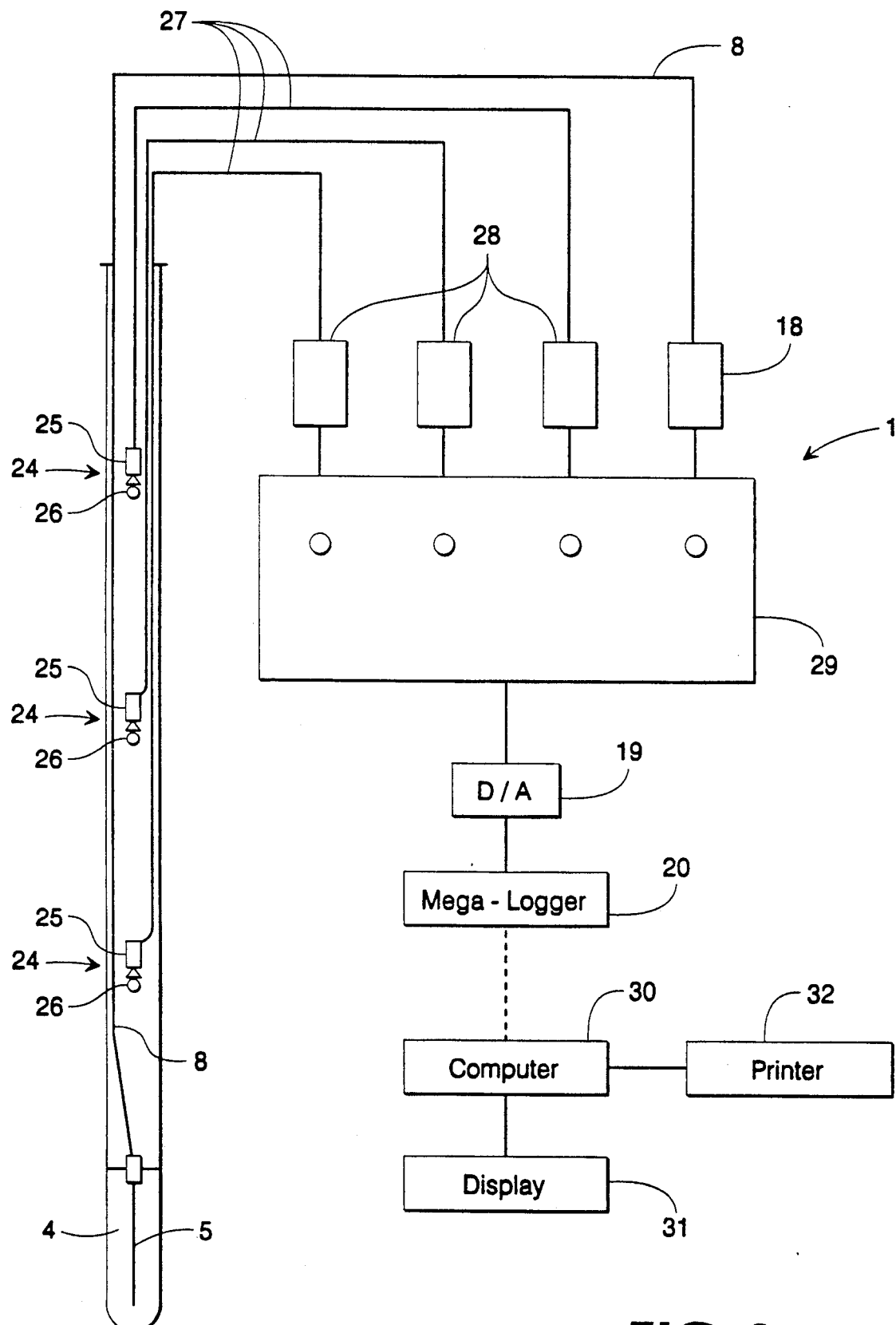
FIG. 3 is a schematic illustration of another embodiment of the manometer.

In the version of the device 1 illustrated in FIG. 3, the catheter 2 has three pressure sensing elements 24 with piezo crystals 25 besides the pressure sensor with the optical fiber 5. The pressure in the oesophagus acts upon the piezo crystals 25 via openings 26 in the catheter 2. Each of the piezo crystals 25 is connected via electrical lines 27 to measuring devices 28. Although in FIG. 3 only one electrical line 27 is shown for each piezo crystal 25, in fact two electrical lines 27 are provided for each. The measuring devices 28 for the three pressure sensing elements 24 are parallel with each other and wired to the directional detector and counter 18 for the optical fiber 5. A common digital-to-analog converter 19 is provided for all measuring devices 28, and the directional detector and counter 18. For this purpose, a multiplexer 29 is connected ahead of the digital-to-analog converter 19. The multiplexer 29 reads in sequentially the readings from the pressure sensing elements 24 and those from the pressure sensor formed by the optical fiber 5. Accordingly, the readings are stored sequentially in the data memory 20. A computer 30, with a display 31 and a printer 32, can be connected to the data memory 20 for evaluating the readings.

Figure 4:
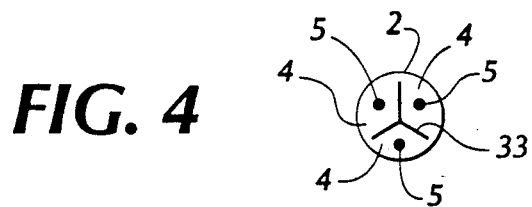
FIG. 4 is a cross-section of another embodiment of the catheter used with the manometer of FIG. 1, FIG. 5 comprises a graph of measurements taken during operation from the version of the manometer according to FIG. 4.

The detail of the device for the manometric measurement of the oesophagus illustrated in FIG. 4 reproduces a cross-section through the tip of the catheter 2 in a version with three optical fibers 5 arranged parallel with each other. Each of the optical fibers is embedded in base material 4. A less elastic support 33 is provided between the optical fibers. The support 33 reduces the coupling among the optical fibers 5. The asymmetry of the oesophagus sphincter can be resolved using the version of the catheter 2 illustrated in FIG. 4.

Figure 5:
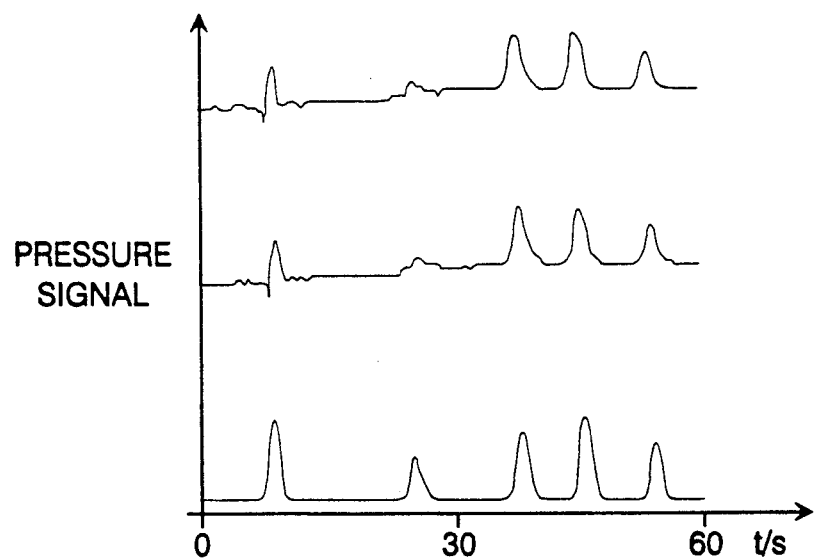

The result of a simulated examination is presented in FIG. 5. Reproduced here are the signals caused by a predetermined pressure progression represented in the basal line using two pressure sensors with optical fibers arranged parallel with each other. It can be seen that the pressure sensors react in a reproducible way to the various pressures without any significant time delay. The coincidence of the signals from the two pressure sensors in this case is explained by a completely symmetrical experimental arrangement which does not correspond to any natural oesophagus sphincter.

Figure 6:
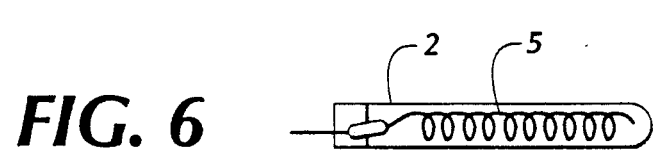
FIG. 6 is a detail of another version of the catheter.

The detail illustrated in FIG. 6 reproduces the tip of the catheter 2 in a further version of the device. Here, the optical fiber is wound around the longitudinal axis of the catheter in helical form. In this way, a relatively long section of the optical fiber 5 is able to be inserted into the area of the oesophagus sphincter. With this arrangement the pressure sensor reacts very sensitively to exogenous force effects.

While the foregoing describes preferred embodiments of the invention, it will be understood by those skilled in the art that variations and modifications thereof can be made without departing from the spirit and scope of the invention as described by the following claims.

I claim:

1. A device for manometric measurement of the oesophagus (21) comprising a catheter (2) having a pressure sensor, and a recording unit (3) having a light source (9) for emitting monochromatic and coherent light and a counting unit for counting light pulses, wherein the pressure sensor further comprises a pliable optical fiber (5) having first and second ends embedded in an elastic base material (4) and is constructed as a Fabry Perot measuring section which is connected to the recording unit by a fiber-optic light guide (8), wherein said first end (6) of the optical fiber (5) is metal-coated and the second end (7) is partially metal-coated and is connected to the fiber-optic light guide (8), whereby the fiber-optic light guide (8) conveys the light emitted from the light source (9) to the optical fiber (5) and conveys a return light pulse from the optical fiber to the counting unit (18).

2. The device according to claim 1, wherein the recording unit (3) further comprises a data memory (20) and is constructed so as to be portable.

3. The device according to claim 1, wherein the recording unit (3) further comprises a temperature probe allocated to the light source (9).

4. The device according to claim 1, wherein the catheter (2) further comprises a plurality of mechanical pressure sensing elements (24) disposed adjacent the optical fiber pressure sensor, whereby the optical fiber pressure sensor measures the pressure of the lower oesophagus sphincter (22) and the pressure sensing elements (24) measure the pressure of the oesophagus (21).

5. The device according to claim 1, wherein the catheter (2) further comprises a plurality of pressure sensors arranged parallel to each other on the circumference of the catheter (2).

6. The device according to claim 5, further comprising a support (33) located inside the catheter (2) between the pressure sensors, wherein said support is made from a material less elastic than the base material (4).

7. The device according to claim 1, further comprising a digitizing facility (19) and a multiplexer (29) connected upstream of a data memory (20).

8. The device according to claim 1 further comprising an adjustable, frequency-dependent filter connected downstream of the counting unit.

9. The device according to claim 1, wherein the second end (7) of the optical fiber (5) is partially metal-coated by the vapor-deposition technique.

10. The device according to claim 1, wherein the optical fiber (5) comprises the single mode type and the fiber-optic light guide (8) is comprised of the multimode type.

11. The device according to claim 1, wherein optical fiber (5) is wound in helical form around the longitudinal axis of the catheter (2).

12. A device for manometric measurement of the oesophagus comprising:
- a pressure sensing catheter;
- a light source for providing monochromatic and coherent light to said catheter;
- a light guide for transmitting light between said catheter and said light source;
- a counting unit for receiving light and counting light pulses;
- said catheter including a pliable optical fiber embedded in an elastic base material and constructed as a Fabry Perot measuring section optically connected to said counting unit via a fiber-optic light guide, with one end of the optical fiber being metal coated and the other end being partially metal coated;
- whereby the fiber optic light guide conveys light from the light source to the optical fiber and conveys light pulses from the optical fiber to the counting unit.

* * * * *